United States Patent [19]

Knight

[11] Patent Number: 5,741,235
[45] Date of Patent: Apr. 21, 1998

[54] RETENTION DEVICE FOR MEDICAL DRAINAGE TUBES AND BILLARY STENTS

[76] Inventor: John R. Knight, 23 Hornbeck Ridge, Poughkeepsie, N.Y. 12603

[21] Appl. No.: 741,405

[22] Filed: Oct. 29, 1996

[51] Int. Cl.⁶ ............................................. A61M 5/32
[52] U.S. Cl. ........................... 604/174; 604/96; 604/175; 128/DIG. 26
[58] Field of Search ................................ 604/96, 97, 98, 604/174, 175; 128/DIG. 26

[56] References Cited

U.S. PATENT DOCUMENTS

| | | | |
|---|---|---|---|
| 4,327,720 | 5/1982 | Bronson et al. | 604/97 X |
| 4,341,210 | 7/1982 | Elam | 604/97 X |
| 4,649,913 | 3/1987 | Watson | 604/174 X |
| 4,863,438 | 9/1989 | Gauderer et al. | 604/175 X |
| 5,267,969 | 12/1993 | Hirsch et al. | 604/174 |
| 5,419,765 | 5/1995 | Weldon et al. | 604/96 |
| 5,445,615 | 8/1995 | Yoon | 604/96 |
| 5,540,715 | 7/1996 | Katsaros et al. | 604/96 X |
| 5,556,385 | 9/1996 | Andersen | 604/174 |

*Primary Examiner*—Sam Rimell
*Assistant Examiner*—Robert V. Racunas
*Attorney, Agent, or Firm*—James T. Sullivan

[57] ABSTRACT

A retention device is presently disclosed for attaching and maintaining the positioning of a transcutaneous drainage tube in a patient without the use of suturing. The retention device is structurally configured to accommodate a drainage tube. Further, the retention device has a small tube and at least one pair of inflatable discs. The tube is positioned such that one of the discs in the pair of discs is located interior the epidermis while the other disc in the pair of discs is located exterior the epidermis. As the tube and discs are inflated, the pair of discs act as a grommet for securing the retention device to the epidermis. The tube is filled with a sterile, medically bio-inert saline solution at a point exterior the epidermis. Further, the retention device also has a flexible disc for holding a sterile dressing proximate the insertion position for the drainage tube. The retention device is positionally maintained without the need of suturing or other invasive connecting devices. The avoidance of invasive connections provides greater comfort, less pain and a reduced chance of additional problems for the patient. This also can reduce the expense of the surgery and the requirement for additional insurance coverage.

2 Claims, 3 Drawing Sheets

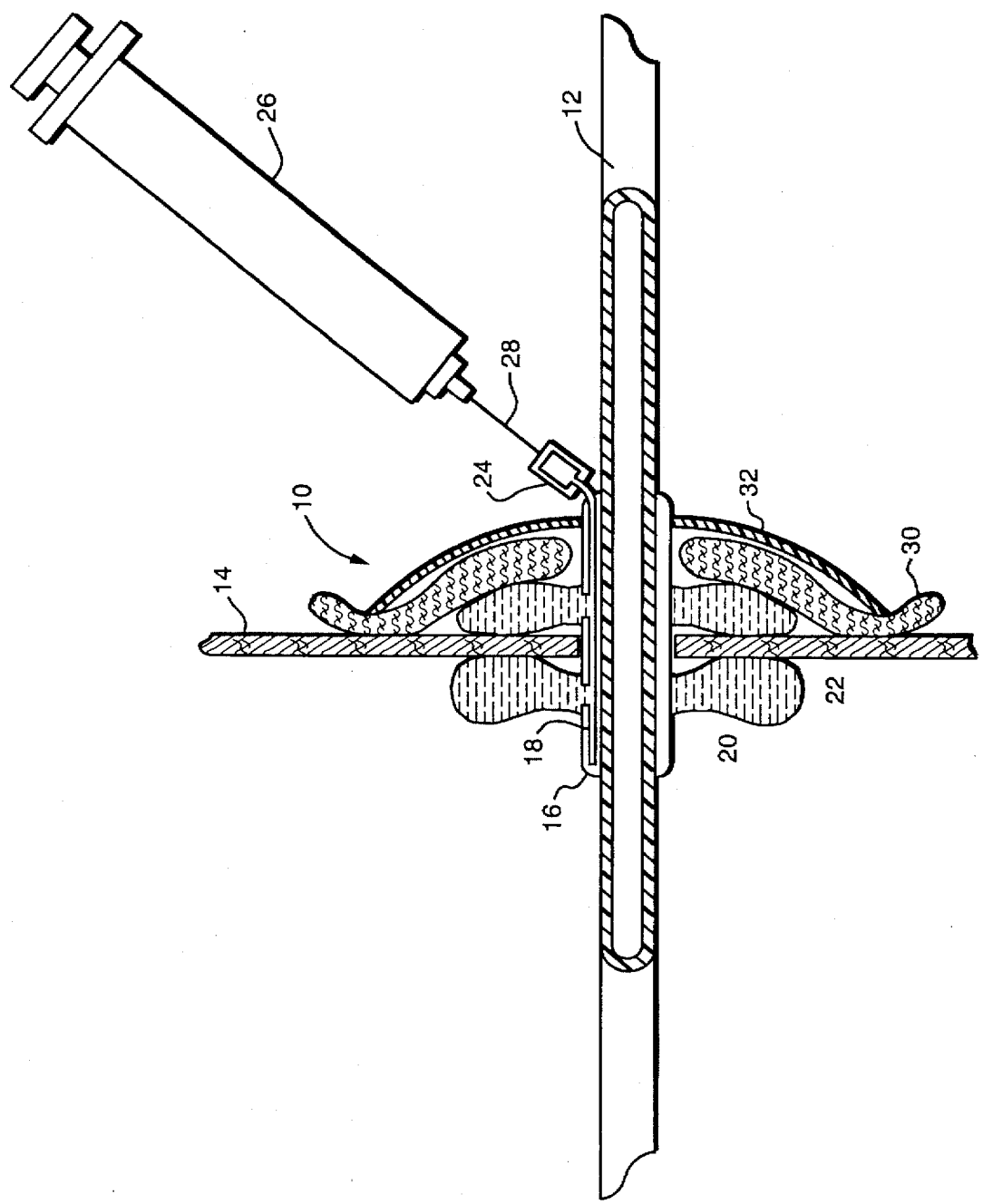

RETENTION DEVICE FOR MEDICAL DRAINAGE TUBES AND BILLARY STENTS

FIELD OF THE INVENTION

The present invention relates to a device for maintaining a transcutaneous drainage tube in a user host, particularly for eliminating a sutured connection between a user host and the drainage tube.

BACKGROUND OF THE INVENTION

Modern medicine, particularly internal surgery, has become more commonplace and quicker. In the past, internal surgery was a more complicated procedure, the recovery was slower and the procedure required long periods of hospitalization with patients attached to machines or other post surgical apparatus. Today, many surgeries allow a patient to be more mobile after the surgery. However, the patient may be required to be installed with certain types of connecting devices allowing the patient to be hooked and unhooked from different medical apparatus. In particular, certain abdominal cavity surgeries require the patient to be installed with a transcutaneous drainage tube that permits the patient to expel waste from their body. The drainage tube, or biliary stent, is internally connected to a patient's organ that has waste to be removed. Such a connection may be, for example, to the gall bladder or, after its removal, through the liver into a bile duct, wherein the distal portion of the drainage tube extends through the patients epidermis to the exterior environment. This allows the removal of toxic waste from a patient by a machine which avoids excess waste accumulating in the patient.

In the past, the position of the drainage tube has been maintained via sutures and tapes to the patients body. The process of suturing is painful and can lead to infection if done improperly. Further, as the patient moves about, the drainage tube is likely to come in contact with foreign matter such as furniture, other persons or the patient themselves. This contact causes the drainage tube to be pulled and pushed which creates extreme amounts of pain for the patient. In severe cases, the sutures can be ripped causing dangerous bleeding and/or infection. Furthermore, patients often suffer irritation and allergic reaction to the tape used to hold dressings for the sutured drainage tube.

The prior art fails to address the problems with suturing transcutaneous drainage tubes to the epidermis of the patient. Further, the prior art fails to recognize any easier and more efficient means to attach and maintain the relative positioning of the transcutaneous drainage tube.

SUMMARY OF THE INVENTION

A retention device is presently disclosed for attaching and maintaining the positioning of a transcutaneous drainage tube in a patient without the use of suturing and taping.

In one illustrative embodiment, the retention device is structurally configured to accommodate a drainage tube. Further, the retention device has a small tube sized and configured to allow a drainage tube to pass therethrough and, in the preferred embodiment, at least one pair of inflatable discs. The tube is positioned such that a first of said inflatable discs from the disc pair is located interior the patient's epidermis while a second disc in the disc pair is located exterior the patient's epidermis and opposite the first of said discs. When the retention device is located in position and the discs are inflated, the pair of discs acts as a grommet for securing the retention device in the position where it passes through the patient's epidermis. The tube is inflated when it is filled with a sterile, medically bio-inert inflation medium such as saline solution from an inflation/deflation valve exterior the epidermis. In another illustrative embodiment, the retention device also has a flexible disc for holding a sterile dressing proximate the insertion position for the drainage tube.

Features of the invention include provision of a retention device that is positionally maintained without the need of suturing or other invasive connecting devices. The avoidance of invasive or painful connections provides greater comfort, less pain and a reduced chance of additional problems for the patient. Further, this can reduce the expense of the surgery and the requirement for additional insurance coverage.

These and other features and advantages of the present invention will be more clearly understood with reference to a detailed description of an illustrative embodiment taken in conjunction with the accompanying drawings in which:

DESCRIPTION OF THE DRAWINGS

FIG. 3 illustrates a sectional view of retention device according to the present invention with the inflatable discs totally inflated.

DETAILED DESCRIPTION

Figure 1:
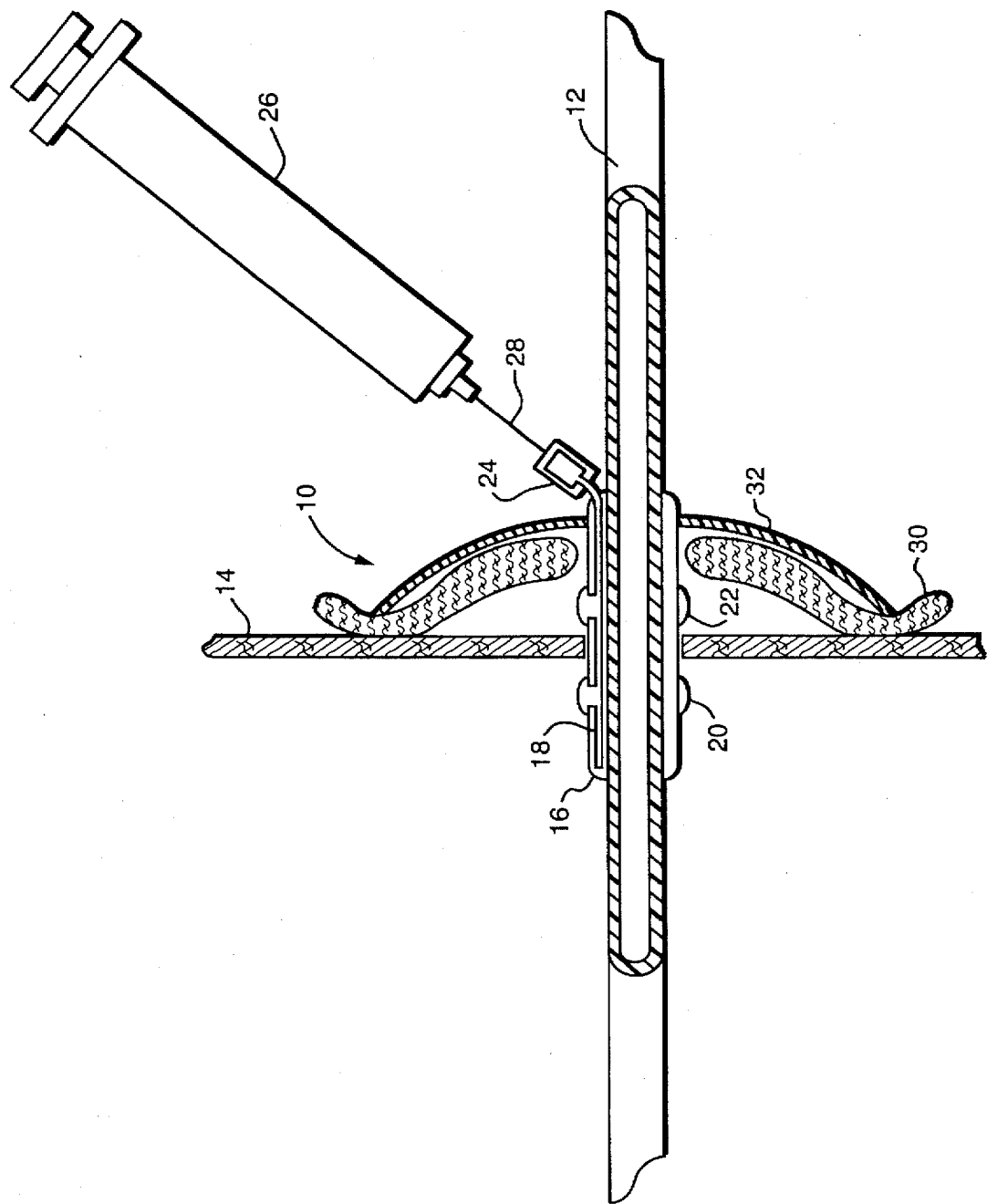
FIG. 1 illustrates a sectional view of retention device according to the present invention with the inflatable discs in their deflated state.
Figure 2:
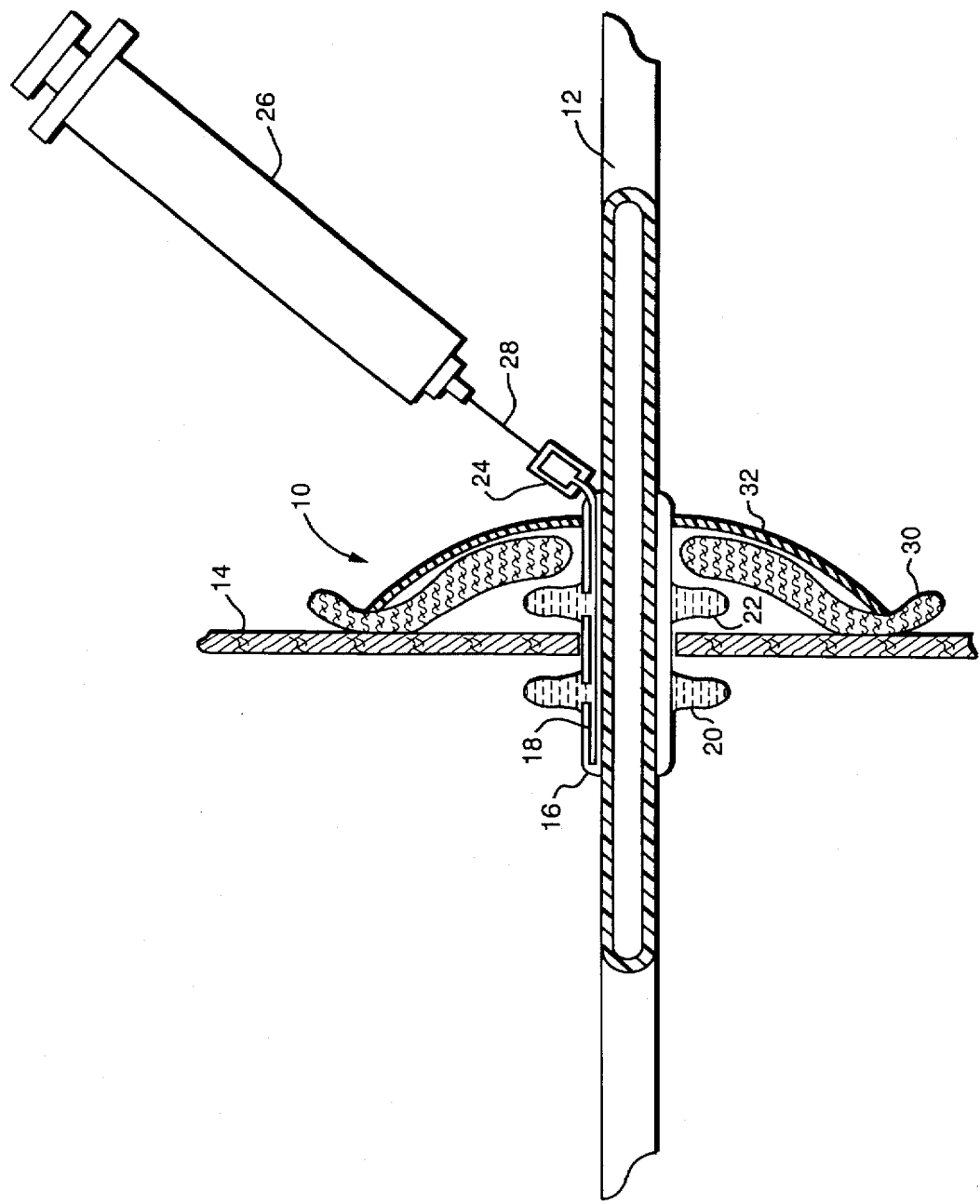
FIG. 2 illustrates a sectional view of retention device according to the present invention with the inflatable discs partially inflated.

Referring to FIGS. 1, 2 and 3, a preferred embodiment of a retention device 10 is illustrated for maintaining the positioning of a transcutaneous device 12 though a patients epidermis 14. In the embodiment described hereafter, the transcutaneous device 12 will be described as a transcutaneous drainage tube. However, it is understood that the invention described hereinafter is capable of positioning and retaining any type of transcutaneous device, including infusion as well as drainage tubes.

The retention device 10 comprises a semi-rigid transcutaneous housing 16, which is sized and shaped to allow the drainage tube 12 to pass therethrough and which protects the drainage tube 12 from being squeezed, kinked, buckled or crushed at the point where it exits from a patient's body. The transcutaneous housing 16 comprises a device positioning/retention means 18, which includes at least one inflatable disc for holding the device in position. In the preferred embodiment, at least one pair of inflatable discs 20 and 22 is used.

The device positioning/retention means 18, with its inflatable discs 20 and 22 may be fashioned from a single piece of non-permeable material which may formed together to provide an enclosed structure. However, the retention device 10 may also be manufactured separately and joined to in such a manner to form the positioning/retention means 18 in a sealed manner. In one embodiment, the non-permeable material permits the positioning/retention means 18 to be capable of repeated inflation and deflation cycles. Thus, a single positioning/retention means may be removed for cleaning, examination or the like and reinserted into a patient's body.

An inflation/deflation valve 24 is included and communicates with the positioning/retention means 18. In a simple embodiment, the valve 24 is a self-sealing plug, which is made out of rubber or other like material that will allow a hypodermic needle to penetrate therethrough to allow a source of inflation medium to be introduced into the positioning/retention means 18. When the device is not connected to a source of the inflation medium, the valve 24 self-seals to prevent the escape of the inflation medium from the positioning/retention means 18.

In the preferred embodiment, when the retention device placed in its proper position where it passes through the patients epidermis, a first inflatable disc 20 of the disc pair is located interior the patient's epidermis. The second inflatable disc 22 of said disc pair is located exterior the patient's epidermis. The positioning/retention means 18 is then inflated using a syringe 26, having a needle 28. The syringe 26 is filled with a medically bio-inert inflation medium such as a sterile saline solution. The needle 28 is inserted into the valve 24 by exerting pressure upon the needle in a manner which causes the needle 28 to penetrate the valve 24. The inflation medium is then injected from the syringe 26, through the needle 28, and into the positioning/retention means 18, which causes the pair of inflatable discs 20 and 22 to expand.

As the pair of discs 20 and 22 expand, they abut the epidermis 14 forming a secure fit, like that of a grommet, between the retention device 10 and the epidermis 14. This provides a structure that is securely fastened to a patient and ensures a stable attachment for allowing the drainage tube 12 to pass therethrough.

The positioning/retention means 18 also retains the transcutaneous drainage tube 12 in position within the retention device 10. When the pair of discs 20 and 22 are inflated, their inner circumferences exert pressure upon the drainage tube about its circumference where it passes through the retention device 10. Simply put, the inflatable discs 20 and 22 squeeze the drainage tube, which prevents it from sliding in or out of the retention device.

Further, a sponge dressing 30 may held in place around the point of entry of the retention device 10 and drainage tube 12 by a flexible disk 32. The sponge dressing 30 assists in preventing dirt or other particulate matter from infecting the open area.

Although a semi-rigid material has been disclosed for the housing, other materials including plastics and various medically acceptable composite materials can be used so long as their particular resilience complies with the needs of the invention. In fact, in another embodiment of the invention, the housing is replaced by a flexible, inflatable cylindrical bladder, which cooperates with the inflatable discs that inflate to hold the device in position. In this embodiment, the entire device can be inflated and deflated. The inflatable bladder holds the drainage tube in position by squeezing it around its circumference. This embodiment more closely approximates the configuration of a flexible, inflatable grommet, which, once it is inflated is semi-rigid.

Further, various shaped housings can be used including cylindrical shaped housings.

Many types of non-permeable materials can be used, such as certain plastics or rubbers. However, other materials can also be used so long as their inherent physical characteristics comply with the necessary limitations of being non-permeable and capable of being expanded to form the inflatable discs while being resilient enough to deflate when the saline is removed.

Although the present invention has been described with respect to illustrative embodiments thereof, workers skilled in the art will recognize that various other modifications, additions and/or omissions may be made in form and detail without departing from the spirit and scope of the invention.

What is claimed:

1. An apparatus for maintaining the position of a transcutaneous device comprising a transcutaneous inflatable bladder, said inflatable bladder sized and shaped to allow a transcutaneous device to pass therethrough, said inflatable bladder comprising at least one pair of inflatable discs, a fist disc or said disc pair located interior a patient's epidermis and a second disc of said disc pair located exterior said patient's epidermis and opposite said first disc and a means for inflating said disc pair with a bio-inert medium such that when said discs are inflated, they abut the epidermis and form a secure grommet-like fit to hold said transcutaneous device in position.

2. An apparatus for maintaining the position of a transcutaneous device according to claim 1 wherein said bio-inert medium is a sterile saline solution.

* * * * *